(12) United States Patent
Marshall et al.

(10) Patent No.: US 6,666,849 B1
(45) Date of Patent: Dec. 23, 2003

(54) DOSE SETTING DEVICE FOR MEDICAL INJECTORS

(75) Inventors: Jeremy Marshall, Oxford (GB); Paul E Jansen, Carmel, IN (US)

(73) Assignees: Owen Munford Limited, Oxford (GB); Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/485,493

(22) PCT Filed: Jun. 11, 1999

(86) PCT No.: PCT/GB99/01861
§ 371 (c)(1),
(2), (4) Date: Oct. 2, 2000

(87) PCT Pub. No.: WO99/64092
PCT Pub. Date: Dec. 16, 1999

(30) Foreign Application Priority Data

Jun. 11, 1998 (GB) .............................................. 9812472

(51) Int. Cl.[7] .......................... A61M 37/00; A61M 5/28; A61M 5/00
(52) U.S. Cl. ......................... 604/246; 604/207; 604/131
(58) Field of Search ........................ 350/116; 604/207, 604/131, 68, 153, 506, 246, 211, 218; 623/1.13; 128/218

(56) References Cited

U.S. PATENT DOCUMENTS

| 4,178,071 A | * | 12/1979 | Asbell ........................ 359/442 |
| 5,114,406 A | | 5/1992 | Gabriel et al. |
| 5,320,609 A | | 6/1994 | Haber et al. |
| 5,569,214 A | * | 10/1996 | Chanoch ...................... 604/207 |
| 5,938,642 A | * | 8/1999 | Burroughs et al. .......... 604/208 |
| 6,221,046 B1 | * | 4/2001 | Burroughs et al. .......... 604/153 |
| 6,277,101 B1 | * | 8/2001 | Kirchhofer et al. .......... 604/208 |

FOREIGN PATENT DOCUMENTS

| EP | 0 268 191 | 5/1988 |
| EP | 0 702 971 | 3/1996 |
| WO | WO 96/32973 | 10/1996 |

* cited by examiner

Primary Examiner—Brian L. Casler
Assistant Examiner—Roz Ghafoorian
(74) Attorney, Agent, or Firm—Young & Thompson

(57) ABSTRACT

A self-use medical injector has a knob at the rear end of a barrel which is rotated from a zeroed position to set the dose and which rotates back again, to the zeroed position, when the injector is fired. A scale is provided on the knob (2) or barrel (1) and a datum mark or indicator on the barrel or knob co-operates with the scale. There is a raised stud (3, 11, 12, 16) providing the indicator or the zero mark of the scale. An annular member (4, 10, 14, 17) fitted over the knob if the stud is on the barrel or over the barrel if the stud is on the knob, has a projection (9, 12, 15, 18) which is registered with a mark on the scale corresponding to the required dose. This projection abuts the stud when the knob is rotated and thus sets the knob for the correct does.

13 Claims, 1 Drawing Sheet

DOSE SETTING DEVICE FOR MEDICAL INJECTORS

BACKGROUND OF THE INVENTION

This invention concerns a dose setting device for self-use medical injectors of the kind having a knob at the rear end which is rotated, before use, by an amount that determines the dose that is to be dispensed. Generally, such a knob is knurled or ribbed for a good grip and when rotated it clicks round over a ratchet mechanism. A sequence of numbers around its periphery indexes past a datum mark on the barrel of the injector, the user ceasing to rotate the knob when the number representing the required dose registers with that mark. The mark is often a raised stud, of arrowhead form for example. When the injector is fired, the knob is released and is returned to its initial position with zero opposite the mark. Such an injector is sold under the Registered Trade Mark AUTOPEN.

OBJECT OF THE INVENTION

While it is commercially sensible to have an injector capable of being set to dispense a wide range of doses, each individual user is likely to be prescribed a set dose, and therefore the knob of his injector is always rotated the same amount before each injection. It is the aim of this invention to make the pre-setting operation easy and almost automatic every time.

SUMMARY OF THE INVENTION

According to one aspect of the present invention there is provided a dose setting device for medical injectors of the kind having a rotary dose setting knob at the rear end of a barrel that can be indexed around from a zeroed position to bring an indicator opposite a mark on a scale, the device comprising an annular member adapted to fit retentively over the dose setting knob in any of a plurality of relative rotational positions each corresponding to a selected dose, and having an abutment which can co-operate with a raised stud on the barrel, rotation of the knob for dose setting being arrested by the abutment meeting the stud with the indicator opposite the selected dose mark.

In the preferred form the annular member is the mouth portion of a cup that press fits over and covers the knob.

Conveniently the scale is on the knob and the annular member is adapted to leave at least part of the scale visible.

However, it is possible for the annular member to be adapted for the scale being on the barrel, the stud being at the zero point thereof, and the indicator being on the knob.

According to another aspect of the present invention there is provided a dose setting device for medical injectors of the kind having a rotary dose setting knob at the rear end of a barrel that can be indexed around from a zeroed position to bring an indicator opposite a mark on a scale, the device comprising an annular member adapted to fit retentively over the rear end of the barrel in any of a plurality of relative rotational positions each corresponding to a selected dose, and having an abutment which can co-operate with a raised stud on the knob, rotation of the knob for dose setting being arrested by the stud meeting the abutment with the indicator opposite the selected dose mark.

The annular member is adapted for the scale being on the knob, the stud being at the zero point thereof, and the indicator being on the barrel.

Alternatively, the scale may be on the barrel, in which case the annular member will preferably be adapted to leave at least part of the scale visible.

When the annular member is so adapted, whether it is on the knob or the barrel, it may be opaque, except for a window through which the selected dose mark may be seen.

Alternatively, the annular member could be a unitary moulding of transparent plastics material, with a short section thickened into a magnifying lens for placement over the selected dose number.

In either case the indicator is conveniently provided is by the stud and the abutment projects from the annular member immediately adjacent the window or lens.

BRIEF DESCRIPTION OF THE DRAWINGS

For a better understanding of the invention some embodiments will now be described, by way of example, with reference to the accompanying drawing, in which.

DETAILED DESCRIPTION OF THE INVENTION

Figure 1:
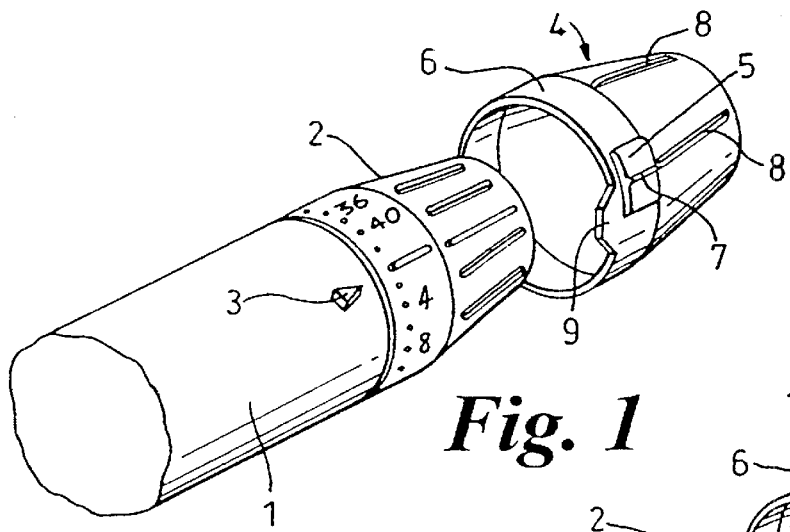
FIG. 1 is a perspective view of a dose setting device in conjunction with the rear end of a self-use medical injector.

The injector of FIG. 1 has a barrel 1 at the rear end of which there is a ribbed knob 2 of generally frusto-conical form. Its base is adjacent the barrel, and around it is printed a sequence of numbers or a scale representing the dose to be dispensed. Pre-use, from a position in which the zero mark of the scale is in registry with an arrowhead stud 3 on the barrel 1, the knob is clicked round until a selected number comes opposite the stud 3.

A cup-like adaptor 4 is press fits over the knob 2 with the letter zeroed. It is a unitary moulding of transparent plastics, and a short section 5 of its skirt 6 is thickened and shaped to form a magnifying lens across the centre of which, in an axial direction, runs a fine rib 7 forming a "hairline". The lens is clear, but the rest of the adaptor 4, and in particular the skirt 6, may be frosted or opaque. When placed over the knob 2, therefore, the number below the lens 5 is clear and magnified while the other numbers are relatively obscure or invisible. Alternatively, there could just be an open window instead of the lens.

The adaptor 4 is formed with external ribs 8 for a good grip, and a trapezoidal lug 9 projects axially from the base of the skirt 6, one sloping side terminating at the skirt 6 directly in line with the rib 7.

The adaptor 4 is fitted so that the lens 5 is over the number representing the required dose. It is not usually possible to print every number (they would be too small if this were done) and so the user may have to interpolate, bringing the rib 7 to a position between two numbers, the lens 5 being circumferentially long enough to show two. The knob 2 is then rotated, through the intermediary of the adaptor 4, until the lug 9 abuts the side of the stud 3, bringing the rotation to a halt. The required dose number or mark is then directly opposite the stud 3 and the injector is correctly set.

When fired, the knob is rotated back again, bringing its zero mark opposite the stud 3. For subsequent injections the procedure is repeated, the same dose being set each time by virtue of the adaptor 4.

Figure 2:
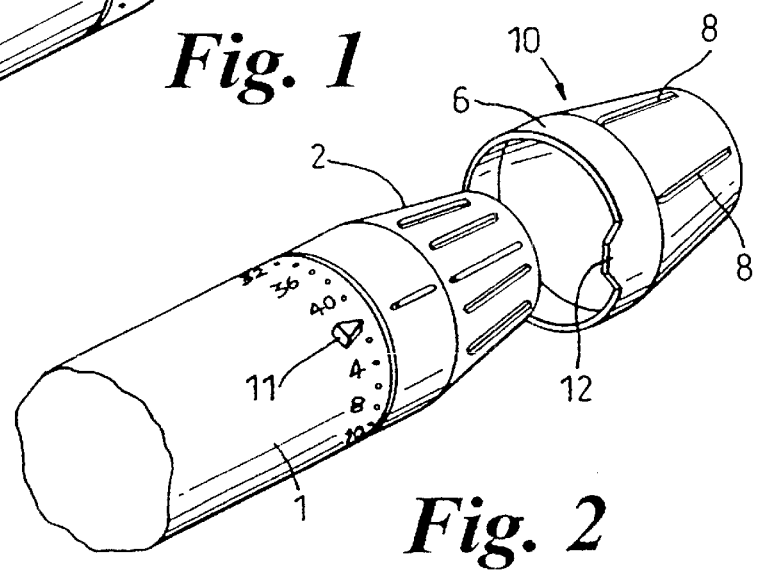
FIG. 2 is a perspective view of another dose setting device in conjunction with a different injector.

Some injectors have the dose numbers or scale on the barrel and a datum mark or indicator on the knob. FIG. 2 shows an adaptor 10 suitable for such an injector, with a raised arrowhead stud 11 at the zero position of the scale. The adaptor has a projection 12 on its skirt similar to the lug 9, and it is fitted with this projection registering with a selected number on the barrel. However, that number does not represent the required dose: with a 360° scale, the required dose number is subtracted from the highest number on the scale and the result is the number against which the projection is aligned. There need be no magnifying lens on the main part of the adaptor, but the skirt will preferably be transparent so that the datum mark or indicator can be seen whatever the positioning of the adaptor on the knob. The projection 12 can be formed as a magnifying lens to enhance the number on the barrel over which it lies.

Figure 3:
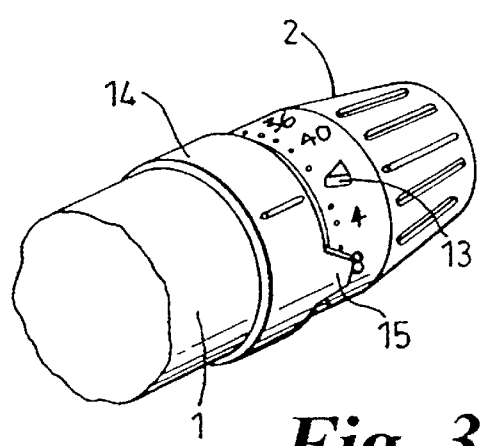
FIG. 3 is a perspective view of a further dose setting device fitted to a third injector.

In a Third embodiment, as shown in FIG. 3, the dose scale is again on the knob but the knob has a raised arrowhead stud 13 at the zero position and the barrel just has a datum mark or indicator. The adaptor 14 takes the form of an annular ring which fits over the mark on the barrel and with a projection 15 extending rearwardly over the base of the knob. The ring will preferably be transparent so that the datum mark or indicator can be seen whatever the position of the ring on the barrel. The projection is can be formed as a magnifying lens to enhance the number over which it lies. But as with FIG. 2, a subtraction has to be done to calculate where the projection should be so that, when the knob is rotated to bring the stud 13 up against the projection 15, the correct dose has been set.

Figure 4:
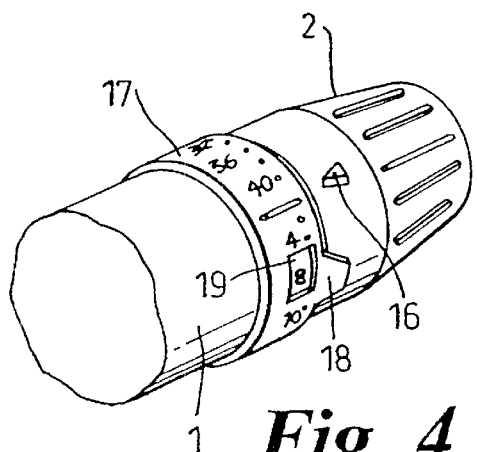
FIG. 4 is a perspective view of yet another dose setting device fitted to a fourth injector.

A further arrangement is shown in FIG. 4 where the dose scale is on the barrel and the knob has a raised arrowhead stud 16 that serves as the indicator. The adaptor 17 is again an annular ring which fits over the dose scale on the barrel and with a projection 18 extending rearwardly over the base of the knob. Conveniently the ring has a window 19 or is formed with a lens similar to that of FIG. 1 so that the relevant part of the scale can be seen; in this embodiment the projection 18 will be positioned adjacent the actual dose number or mark required and no calculation will be necessary.

What is claimed is:

1. A dose setting device for medical injectors of the kind having a barrel with a front and a rear end and a rotary dose setting knob at the rear end of the barrel that can be indexed around from a zeroed position to bring an indicator opposite a mark on a scale, the device comprising an attachable and removable dose determining annular member adapted to be selectively attached on the dose-setting knob to fit retentively over the dose-setting knob in a selected one of a plurality of relative rotational positions each corresponding to a selected predetermined maximum dose, the annular member having an abutment which can co-operate with a raised stud on the barrel, rotation of the knob, together with the attached annular member, for dose setting being arrested by the abutment meeting the stud with the indicator opposite the selected dose mark, thus determining the selected maximum dose and preventing further rotation of the knob beyond the selected dose.

2. A dose setting device as claimed in claim 1, wherein a cup press fits over and covers the knob, and has a mouth portion which defines the annular member.

3. A dose setting device as claimed in claim 1, wherein the scale is on the knob and the annular member is adapted to leave at least part of the scale visible.

4. A dose setting devices as claimed in claim 1, wherein the annular member is adapted for the scale being on the barrel, the stud being at the zero point thereof, and the indicator being on the knob.

5. A dose setting device for medical injectors of the kind having a barrel with a front end and a rear end and a rotary dose setting knob at the rear end of the barrel that can be indexed around from a zeroed position to bring an indicator opposite a mark on a scale, the device comprising an attachable and removable dose determining annular member adapted to be selectively attached over and to fit retentively over the rear end of the barrel in a selected one of a plurality of relative rotational positions each corresponding to a selected predetermined maximum dose, the annular member having an abutment which can co-operate with a raised stud on the knob, rotation of the knob for dose setting being arrested by the stud meeting the abutment with the indicator opposite the selected dose mark, thus determining the selected maximum dose and preventing further rotation of the knob beyond the selected dose.

6. A dose setting device as claimed in claim 4, wherein the annular member is adapted for the scale being on the knob, the stud being at the zero point thereof, and the indicator being on the barrel.

7. A dose setting device as claimed in claim 6, wherein the scale is on the barrel and the annular member is adapted to leave at least part of the scale visible.

8. A dose setting device as claimed in claim 3, wherein the annular member is opaque, except for a window through which the selected dose mark may be seen.

9. A dose setting device as claimed in claim 3, wherein the annular member is a unitary moulding of transparent plastics material, with a short section thickened into a magnifying lens for placement over the selected dose number.

10. A dose setting device as claimed in claim 8, wherein the indicator is provided by the stud and the abutment projects from the annular member immediately adjacent the window or lens.

11. A dose setting device as claimed in claim 7, wherein the annular member is opaque, except for a window through which the selected dose mark may be seen.

12. A dose setting device as claimed in claim 7, wherein the annular member is a unitary moulding of transparent plastics material, with a short section thickened into a magnifying lens for placement over the selected dose member.

13. A dose setting device as claimed in claim 9, wherein the indicator is provided by the stud and the abutment projects from the annular member immediately adjacent the window or lens.

* * * * *